United States Patent [19]
Kluger

[11] Patent Number: 5,478,340
[45] Date of Patent: Dec. 26, 1995

[54] VERTEBRAL COLUMN IMPLANT AND REPOSITIONING INSTRUMENT

[76] Inventor: Patrick Kluger, Heinrich-Hammer-Strasse 12, 7904 Erbach, Germany

[21] Appl. No.: 10,314

[22] Filed: Jan. 28, 1993

[30] Foreign Application Priority Data

Jan. 31, 1992 [DE] Germany ............... 42 02 748.9

[51] Int. Cl.⁶ .................................................. A61B 17/70
[52] U.S. Cl. ............................................................. 606/61
[58] Field of Search ................... 606/105, 53, 54, 606/55, 57, 58, 59, 60, 61, 72, 73

[56] References Cited

U.S. PATENT DOCUMENTS

| | | | |
|---|---|---|---|
| 2,391,537 | 12/1945 | Anderson | 606/54 |
| 2,774,350 | 12/1956 | Cleveland, Jr. | 606/54 |
| 4,386,603 | 6/1983 | Mayfield | 606/105 |
| 4,733,657 | 3/1988 | Kluger . | |
| 4,957,495 | 9/1990 | Kluger | 606/58 |
| 4,987,892 | 1/1991 | Krag et al. | 606/61 |
| 5,219,349 | 6/1993 | Krag et al. | 606/105 |
| 5,254,118 | 10/1993 | Mirkovic | 606/61 |

FOREIGN PATENT DOCUMENTS

| | | |
|---|---|---|
| 0220736 | 5/1987 | European Pat. Off. . |
| 045783A1 | 5/1991 | European Pat. Off. . |
| 0468264 | 1/1992 | European Pat. Off. . |
| 3219575 | 12/1983 | Germany . |
| 3625542 | 11/1987 | Germany . |
| 888968 | 12/1981 | U.S.S.R. ............... 606/61 |
| 1156673 | 5/1985 | U.S.S.R. . |
| 1676605 | 9/1991 | U.S.S.R. . |
| 1685423 | 10/1991 | U.S.S.R. . |
| 2076657 | 12/1981 | United Kingdom ............... 606/59 |

OTHER PUBLICATIONS

P. Kluger "Das Fixateurprinzip an der Rumpfwirbel–säule–. . . "; Fixateur externe–Fixateur interne Springer–Verlag Berlin Heidelberg 1989.

*Primary Examiner*—Tamara L. Graysay
*Attorney, Agent, or Firm*—Spencer, Frank & Schneider

[57] ABSTRACT

An implant for stabilizing the vertebral column, having a longitudinal support and anchoring screws which can be fastened to the latter in an angularly stable manner so that even long-span multi-segmental instabilities can be treated. As the longitudinal support a sectional rod is provided, to which transverse brackets are clamped. The anchoring screws are fastened at an adjustable angle of inclination to a transverse bracket in each case. The transverse bracket comprises a clamping piece and a connector, which are screwed together. The clamping piece has two jaws which form a suitable receiving opening for the preferably cross-sectionally circular sectional rod and are drawn together by a clamping screw. In addition, two repositioning instruments for altering the position of the vertebral bodies during the operation are described, namely a traction instrument and an instrument which can be used as a basis of application for the traction instrument and which creates a connection between two neutral vertebrae.

12 Claims, 4 Drawing Sheets

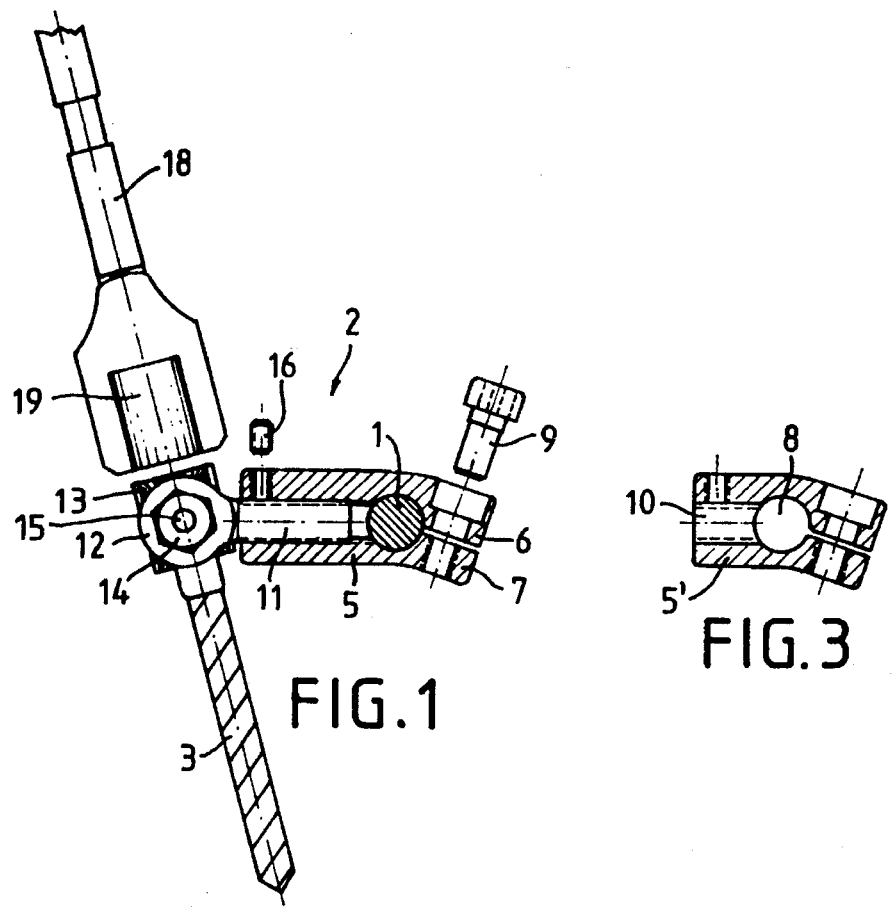
FIG. 1
FIG. 3
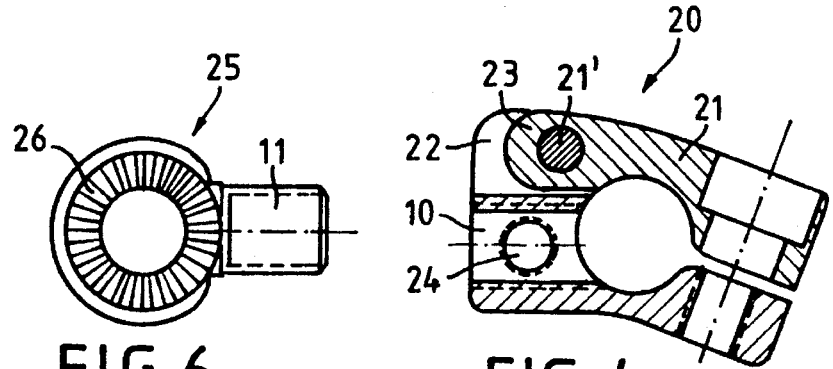
FIG. 6
FIG. 4
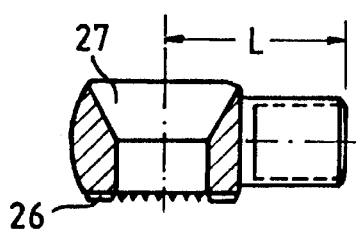
FIG. 7
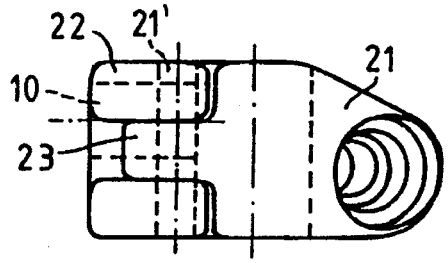
FIG. 5

16,478,340

VERTEBRAL COLUMN IMPLANT AND REPOSITIONING INSTRUMENT

BACKGROUND OF THE INVENTION

The invention relates to an implant for stabilizing the vertebral column, having a longitudinal support and anchoring screws which can be fastened to the latter in an angularly stable manner, and to an associated repositioning instrument.

In the case of all known fixation systems of this type, two longitudinal supports are used which are disposed essentially symmetrically to the longitudinal axis of the vertical column. This applies, in particular, in the case of short-span implants, i.e. those intended to bridge only one vertebral body, such as disclosed in German Patent No. 32 19 575 or according to the paper by P. Kluger from TH. Stuhler "Fixateur extern—Fixateur intern", Springer-Verlag Berlin Heidelberg 1989, pages 36 to 58.

SUMMARY OF THE INVENTION

The object of the invention is to bridge a larger distance and to fix more than just two vertebral bodies in place, i.e. to provide an implant by which even long-span, multi-segmental instabilities and malpositions can be treated.

This object is achieved according to the invention by the fact that, in total, only one longitudinal support is provided in the form of a sectional rod without a specific end configuration, to which transverse brackets are clamped, and the fact that the anchoring screws are fastened at an adjustable angle of inclination to a transverse bracket in each case. The longitudinal support, in particular a round rod, is easily shortened to the required length. The number of transverse brackets and their arrangement on the longitudinal support is optional. As will further be shown, the length of the individual transverse brackets is selectable in small steps and precautions are additionally taken to ensure that also two anchoring screws of a vertebral body, which are screwed in, in a known manner, with clear convergence through the arch roots, can be fitted to the longitudinal support without the corresponding transverse brackets impeding each other.

This implant, which in terms of modular construction can be assembled in various ways, serves for the permanent fixing of an, in principle, optional number of vertebrae to one another in their position achieved by the repositioning instruments. Thereafter, the instrumented vertebral column section can be stiffened by the attachment of bone tissue. The implant is matched perfectly to the varying locality, distance and spatial direction of the anchoring screws. Whilst achieving adequate stability, the quantity of implanted material remains, moreover, relatively small.

Preferably, the transverse brackets comprise in each case a clamping piece and a connector, which are screwed together. The connector has a latching surface exhibiting a central bore for the fixed-angle connection of a known anchoring screw having a corresponding latching surface. The bore axis of the latching surface of the connector must be perpendicular to the threaded shank of the latter. The clamping piece expediently has two pincer-like jaws, which form a suitable receiving opening for the sectional rod. In the case of an embodiment as a ring clip, the two jaws are moulded onto the clamping piece itself, the clamping movement being performed within the framework of the material elasticity. However, the clamping piece can also be advantageously configured in two parts, one jaw being attached in a hinge-like manner. Clamping pieces of this kind do not need to be threaded onto the rod. They can be attached directly to the longitudinal support or retrospectively inserted between already fitted clamping pieces. The screw connection between the clamping piece and the connector is preferably realized such that the clamping piece, on the opposite side of the receiving opening for the sectional rod, is configured as a screw sleeve, i.e. as a threaded bore, which preferably extends perpendicular to the receiving opening. The connector is in this case arranged as a preferably round disk having a latching surface with a radially mounted threaded shank.

For length-matching purposes, the connectors having threaded shanks of suitable length graduations are kept available. By suitable inclination of the transverse bracket, this can be adjusted to the height of the head of the anchoring screw and secured by tightening the clamping screw. The direction of the anchoring screw is determined in the one axis by the angular position of the threaded journal and in the other axis by the relative adjustment of the latching disks.

In order to allow large inclinations of the transverse brackets without their parts on the clamping screw side protruding outwards, it is proposed that the clamping piece should have a bent form, so that the axes of the threaded bore and of the clamping screw are at an oblique angle to each other. In order, moreover, to be able to move two clamping pieces as close up to each other as possible, without hindrance, and thereby receive both anchoring screws of a vertebral body, it is proposed that the axes of the receiving bores for the connector on the one hand and for the clamping screw on the other hand should be mutually offset on the clamping piece in the direction of the sectional rod.

The basis for the repositioning instruments proposed below is provided, e.g. in the case of a lateral bending-out of the vertebral column, by the following problem definition. In order to bend back the vertebral column section in question, tensile forces directed at the concave side of the bending must be applied to the vertebrae or at least to some of them. These forces require a stable counter-bearing outside the wound and suitable traction instruments.

From German Patent Nos. 34 14 374 and 37 11 091, so-called distraction or compression instruments, depending upon their application, are known. These serve to create a mechanical connection between two anchoring screws which are held on removable extension rods, the mechanical connection being situated outside the wound. In this case, the instrumented vertebral column section remains accessible during the operation. By displacement of the movable arm, a compressive or tensile force can be exerted between the two vertebrae in which the anchoring screws are seated. It is proposed that an instrument of this type, comprising a longitudinal member and a fixed arm and an arm which is adjustable in the longitudinal direction, to which arms a support of a receiving hollow element for an extension rod is attached in each case, should be refined by virtue of the fact that the hinge axes run approximately in the plane defined by the arms and run at such an angle of inclination that they intersect in the extension direction on the side facing the longitudinal member. This hinge arrangement enables the longitudinal member to be used as a basis of application for the abovementioned tensile forces, provided merely that the longitudinal member is long enough to form a bridge between the upper and lower vertebral bodies which close off the vertebral column section in question.

Expediently, the hinge axes can exhibit an angle of approximately 30° in relation to the longitudinal member. In order adequately to fix the points of application of the traction instruments, it is further proposed that the longitudinal member of the aforementioned instrument should be a toothed rack, the teeth of which are situated on the side facing away from the arms and are of such a nature, particularly in respect of the interval between them, that hooks fitted to the traction instruments can be inserted between the teeth.

The tensile forces for the repositioning of the intermediate vertebrae must act upon the anchoring screws, whilst at the same time maintaining the spatial angular position of the said screws. In order to achieve this, as the traction instrument a repositioning instrument is proposed exhibiting two sleeves, which are traversed by a spindle and can be drawn together by the screwing movement of said spindle, one of which sleeves exhibiting a hook and the other an arm lying at an angle to the direction of pull, to which arm a receiving hollow element for an extension rod is fitted such that it is adjustable and fixable about an axis perpendicular to the threaded spindle. The necessary degrees of freedom for matching to the direction of the anchoring screw derive from the free rotatability of the angled arm about the spindle axis, from the free rotatability of the extension rod in the receiving hollow element and from the adjustability of the receiving hollow element in relation to the arm.

In the case of this repositioning system, the advantages of the known short-span instrumentation are preserved, namely the redirection of the mechanical connection during the operation to outside the wound, the easily removable extension rods of the individual anchoring screws as repositioning levers and the angularly stable connection of these levers to the arms or draw spindles of the instruments. In the case of this latter connection, correction of the position is maintained in all degrees of freedom.

The permanent implant is advantageously slender and flat, so that fittings are also possible on the upper and central thoracic vertebral column. Further fields of application for the proposed implants and instruments are polysegmental destruction associated with tumors, some serial fractures, degenerative changes and, very particularly, scolioses for the purpose of dorsal derotation spondylodesis (DDS).

BRIEF DESCRIPTION OF THE DRAWINGS

Illustrative embodiments of the invention are described below with reference to the drawing in which, specifically:

FIG. 1 shows the partial longitudinal section of a transverse bracket according to the sectional line I—I, FIG. 3 shows the longitudinal section of a short, one-part clamping piece, FIG. 4 shows the longitudinal section of a two-part clamping piece on a larger scale, FIG. 5 shows the plan view of the clamping piece according to FIG. 4, FIG. 6 shows the front view of a short connector, FIG. 7 shows a partial section of the connector according to FIG. 6.

DESCRIPTION OF THE PREFERRED EMBODIMENTS

Figure 2:
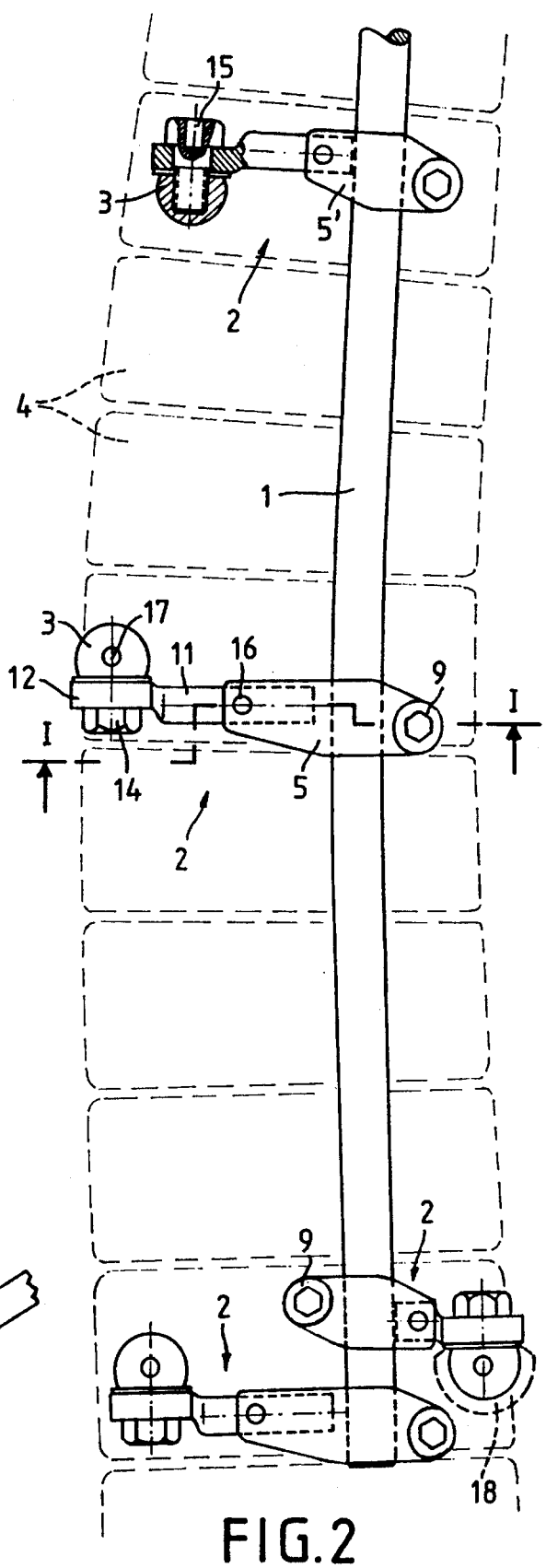
FIG. 2 shows the plan view of a part of an implant for long-span vertebral column fixing.

As represented in FIGS. 1 and 2, the implant comprises a cross-sectionally circular sectional rod 1 having a plurality of transverse brackets 2, to which an anchoring screw 3 is fastened in each case. The sectional rod 1 is cut down to the necessary length beforehand and adapted by bending to the desired course of the vertebral column in order to find space laterally next to the processus spinosus. The vertebral bodies 4 of the observed vertebral column section are represented diagrammatically.

The transverse brackets are clamped by their clamping pieces 5 to the sectional rod 1. For this purpose, two jaws 6 and 7 are moulded onto the clamping pieces, which jaws form a circular cylindrical receiving opening 8 (FIG. 3) for the sectional rod 1 and exhibit a threaded bore with a view to being tightened together by means of a hexagon socket screw 9, the receiving opening 8 being constricted due to elastic deformation such that the clamping piece 5 adheres firmly to the sectional rod 1. On the other side, there is located in the clamping piece 5 and its other embodiments a threaded bore 10 for receiving the threaded shank 11 of a plate-shaped connector 12. As the plan view according to FIG. 2 show, the threaded bore 10 is offset, in relation to the axis of the hexagon socket screw 9, in the direction of the sectional rod 1. The connector 12 has on one side a star-shaped latching surface, which interacts with the latching surface 13 on the flat-topped head of the anchoring screw 3 and guarantees its angular stability. The connection is effected with the aid of a hexagonal cap screw 14, which exhibits, as an assembly aid, a cylindrical holding bore 15. The threaded shank 11 is fixed by means of a stud screw 16 having a hexagon socket. Securing screws 17 are provided on the end face of the anchoring screws 3 and screwed in perpendicular to the axis of cap screws 14 to secure the cap screws.

In a known manner, an extension rod 18 serves for the insertion of the anchoring screws 3 and acts as a lever for the application of the forces, which extension rod can be mounted on the screwhead by the trough-shaped cavity 19 in its thickened lower end section and fixed in place. An extension rod 18 of this kind is indicated in FIG. 1.

In FIG. 3, a clamping piece 5' is represented as a variant, the threaded bore 10 of which is shorter in relation to that found in the clamping piece 5. The aim of this is to create the possibility of also fastening an anchoring screw, with very small spacing, to the sectional rod 1, as can be seen at the bottom right in FIG. 2. This part-section also shows, moreover, that the two anchoring screws of a vertebral body, situated on a common transverse axis, can be gripped by two transverse brackets 2, there still being space to apply the cap of an extension rod 18, which extension rod is indicated by dash-dot lines.

The clamping piece 20 according to FIGS. 4 and 5 differs from the preceding ones by virtue of a hinge-fitted jaw 21. This has a boss 23 disposed between two humps 22 in the clamping piece, an axle pin 21' passing transversely through the said parts. Here, too, the clamping function is assumed by a hexagon socket screw. The threaded bore 10 for the connector, which threaded bore likewise exhibits a transverse bore 24 for a securing screw, is once again eccentrically disposed beneath the hinge joint.

FIGS. 6 and 7 show a different connector 25, which exhibits, on the side lying opposite its latching surface 26, a conical recess 27 for receiving the head of a countersunk hexagon socket screw (not represented). In the example, the threaded shank 11 is extremely short. A supply with larger lengths L in stages should be kept available. The countersunk screws have the advantage of reducing the size of the connecting arrangement and providing it with a smoother surface.

Figure 8:
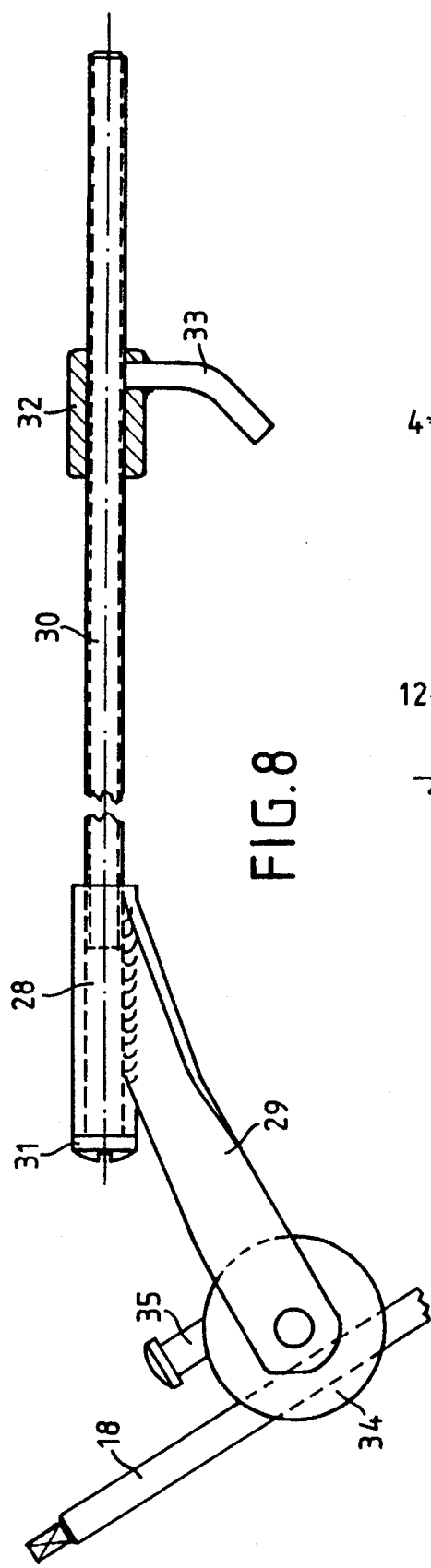
FIG. 8 shows the side view of a traction instrument.

The traction instrument represented in FIG. 8 exhibits a sleeve 28 having a smooth bore and a slanting arm 29 welded thereto. Inserted in the sleeve is a threaded spindle 30, the head 31 of which comes to bear against the face side. Screwed onto the spindle is a threaded sleeve 32 exhibiting a sturdy hook 33. The disk-shaped support 34 of a known cylindrical disk-shaped receiving hollow element 47 is fastened to the slanting arm 29. Said element can be adjusted, by means of interacting latching surfaces 48 and by a ring nut 49 which locks these in place (FIGS. 10 and 11) in angular steps of 6° in relation to the axis of the support 34. In addition, the upper end of an aforementioned extension rod 18 is shown, which extension rod is locked in a tangential bore of the receiving hollow element 47 in the longitudinal direction and can be released by pressing a button 35. This instrument, as will be further explained, serves to apply a tensile force to an anchoring screw.

Figure 9:
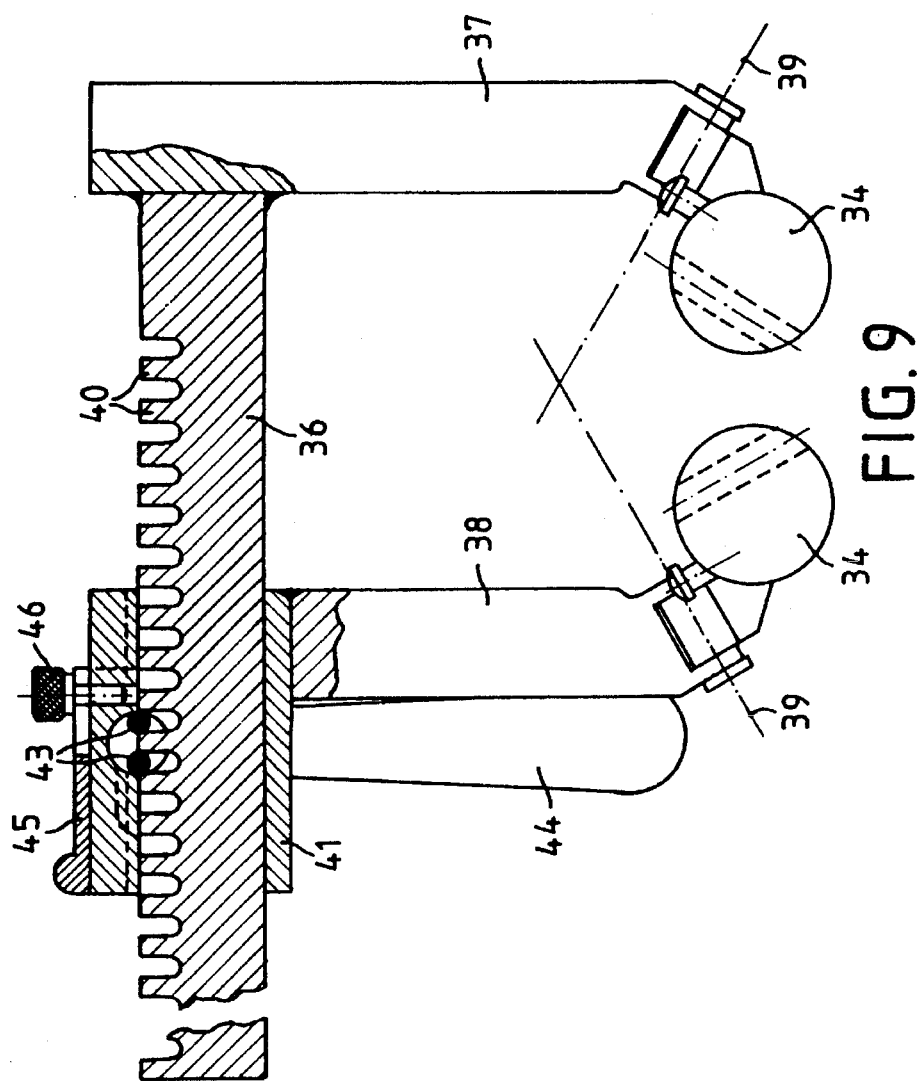
FIG. 9 shows the side view, partly fragmented, of a special distraction instrument which connects the terminal vertebrae and forms the basis of application for traction instruments.
Figure 10:
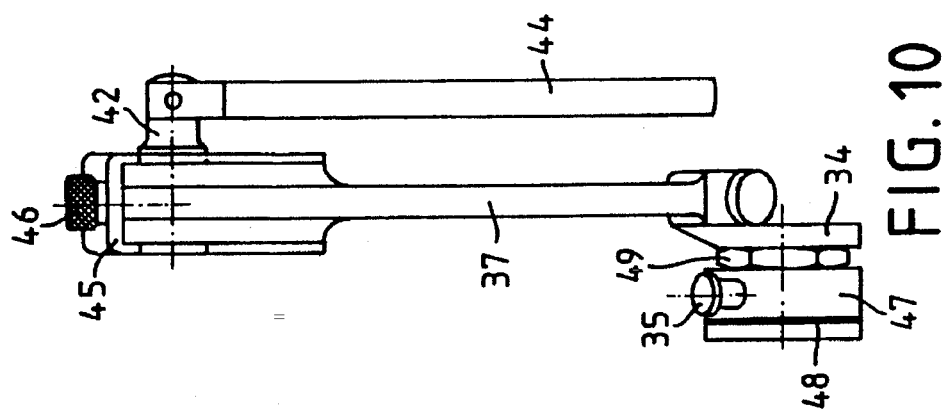
FIG. 10 shows the view of the front of the distraction instrument according to FIG. 9

The distraction instrument according to FIGS. 9 and 10 comprises the basic elements—a longitudinal member 36, a fixed arm 37 and a displaceable arm 38. On the arms there are disposed simple, single-axis joints for the supports 34 of the receiving hollow bodies 47. An essential feature of this instrument consists in the fact that the hinge axes 39 are not mutually aligned but lie at an angle to each other, to be precise such that they intersect in the area between the arms 37 and 38, i.e. the supports 34 are facing each other.

The longitudinal member 36 is a flat rack having scalloped, parallel-flanked teeth 40. The displaceable arm 38 is firmly connected to a rectangular sleeve 41, in which a drive shaft 42 is mounted. The rectangular sleeve comprises, in the thick area of the rack, two parallel round pins 43, which, upon the rotation of the drive shaft, intrude alternately into the tooth gaps. A lengthy toggle 44 serves as an actuating member for the drive system. The rectangular sleeve 41 can be locked in a specific position by means of a slide 45. The slide, for its part, can be secured by means of a stop screw 46.

Figure 11:
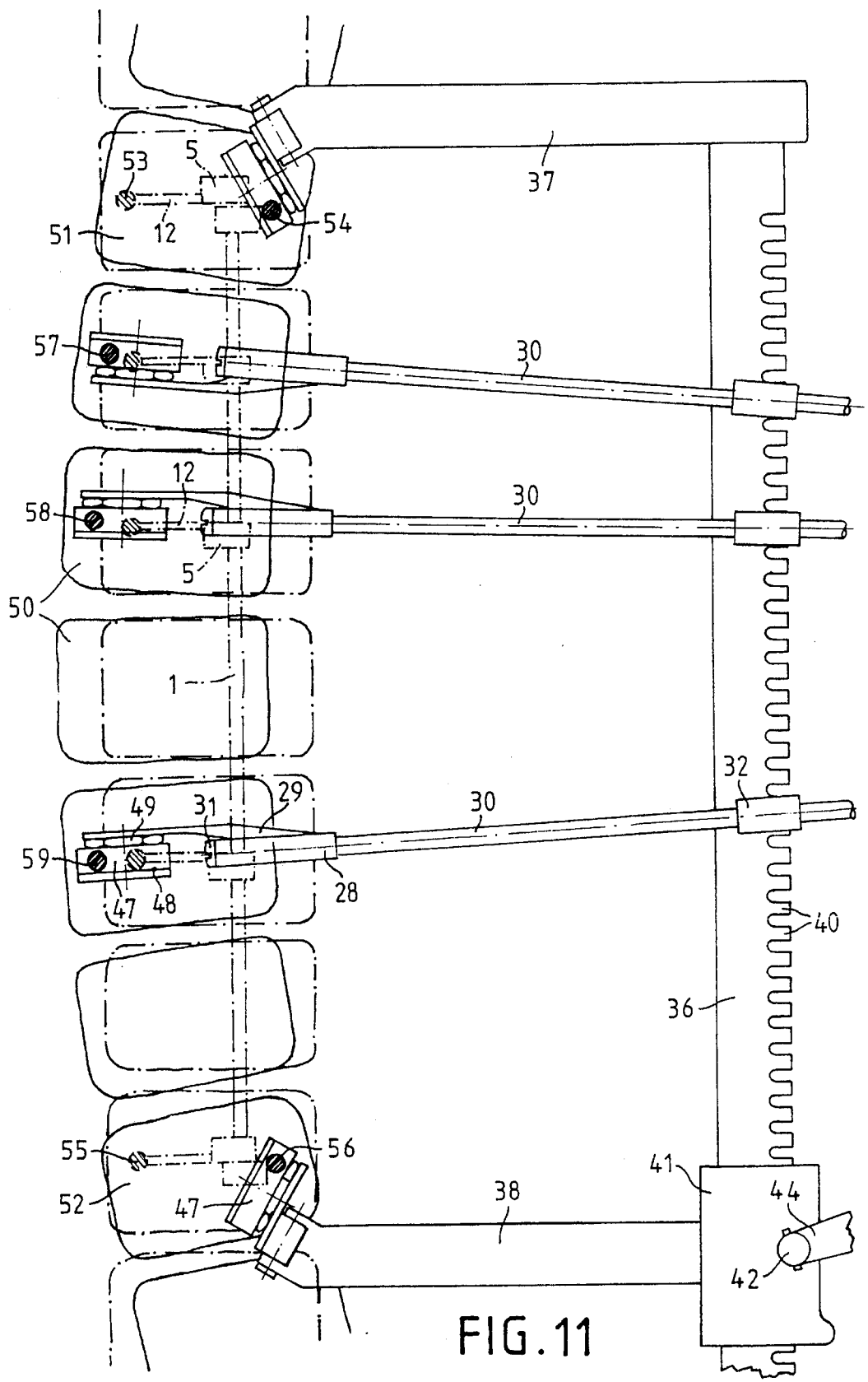
FIG. 11 shows the diagrammatic front view of a typical arrangement during the operation.

FIG. 11 shows diagrammatically, in fully continuous lines, the vertebral bodies 50 of a laterally curved vertebral column section (scoliosis) exposed during the operation. The upper and lower vertebral bodies 51 and 52 are the "neutral" terminal vertebrae of the curved area. They are gripped by the distraction instrument. In the example, two anchoring screws 53, 54 or 55, 56 are inserted in each of these two vertebral bodies 51 and 52. In the operation, extension rods 18 are mounted on all the anchoring screws, including those mentioned below. The extension rods of the screws 54 and 56 are inserted in the receiving hollow elements 47 of the distraction instrument and secured there.

In the example, furthermore, three selected vertebral bodies are provided with anchoring screws 57, 58 or 59. Their extension rods are acted upon by three traction instruments, as represented in FIG. 8. The hooks 33 of these traction instruments are hung over the comb-shaped tooth edge of the longitudinal member 36 of the distraction instrument, which distraction instrument is located on the concave side of the curvature.

Starting from this situation, the traction instruments can be shortened, under the accompaniment of X-ray checks and possible regulating influence upon the angular positions, by rotation of the screws 31. As a result, the displaced vertebral bodies 50 are pulled into the desired straight position, which is indicated in dash-dot representation. In this new position, which initially is fixed only by the instruments, the implant is fitted. Due to the slanting arms 29, the threaded spindles 30 of the traction instruments are situated at a height such that access is not obstructed. The longitudinal rod 1, the clamping pieces 5 and the connectors 12 of the transverse brackets are indicated, likewise in dash-dot representation, in their permanent end position. All in all, in the example, five vertebral bodies are interconnected in this case via seven anchoring screws. Following fitting, the instruments and, finally, the extension rods 18 are removed.

The number of anchoring points in the instrumented vertebral column section is governed by the level of instability. Hence, in the case of fractures or tumorous destruction of individual vertebrae, for example, a large number of anchoring points are needed, whereas, on the other hand, an actually intact, but distorted vertebral column can be held in its position by a small number of anchoring points. Accordingly, a decision must also be taken on whether, in each case, both arch roots of the instrumented vertebrae between the upper and lower terminal vertebrae are to be gripped by anchoring screws. The number of vertebrae which must be acted upon by traction instruments is governed by the type, the extent and the rigidity of the malposition. Finally, it is possible, in addition to a distraction instrument fitted according to FIG. 11 on the concave side, correspondingly to influence a bending of the vertebral column in the same section, in the forward or rearward direction, by means of instruments fitted on the counter-side between further vertebrae. Multi-arched, often twin-arched vertebral column distortions are not infrequent. These can be tackled logically using the same instruments.

I claim:

1. An implant for stabilizing the vertebral column, comprising:

a sectional rod for providing longitudinal support to the vertebral column;

anchoring screws for being fastened to said rod, each said anchoring screw having a head with a bore transverse to a longitudinal axis of said anchoring screw;

transverse brackets each comprising: a clamping piece for being clamped to said rod; and a connector for connecting a respective one of said anchoring screws with said bracket, said clamping piece having a threaded opening and said connector having a bore and a threaded pin fitting into the threaded opening of the clamping piece; and a latching screw engaging the bore of said connector and the transverse bore in the head of a respective anchoring screw for fixing said anchoring screw to said connector at a selectable angle of rotation about the longitudinal axis of the latching screw.

2. The implant as claimed in claim 1, wherein said rod has a circular cross section.

3. The implant as claimed in claim 1, wherein said clamping piece includes two jaws which present a further opening for receiving said rod, a clamping screw arranged to one side of the further opening for drawing said jaws together on said rod, the threaded opening of said clamping piece being arranged at an opposite side of the further opening relative to the clamping screw so that the threaded pin of said connector can be screwed into the threaded opening of the clamping piece perpendicular to the further opening of the clamping piece.

4. The implant as claimed in claim 3, wherein said clamping piece includes a hinge connection for connecting one of said jaws to be pivotable relative to the other of said jaws.

5. The implant as claimed in claim 3, wherein said clamping piece has a bent form and the axes of the threaded opening of the clamping piece and of the clamping screw are at an oblique angle with respect to each other.

6. The implant as claimed in claim 3, wherein the axes of the threaded opening of the clamping piece and of said clamping screw are spaced apart in the longitudinal direction of said rod when said clamping piece is clamped to said rod.

7. The implant as claimed in claim 1, in combination with extension rods adapted to be mounted on the heads of said anchoring screws.

8. The implant as defined in claim 7 in combination with a vertebral column-repositioning instrument for use with said implant, said instrument comprising:

a threaded spindle;

two sleeves mounted on said spindle for being drawn together by a screwing movement of said spindle, one of said sleeves including a hook and the other of said sleeves having an arm lying at an angle to the longitudinal direction of said spindle; and a receiving hollow element adjustably attached to said arm and fixable about an axis perpendicular to said spindle, said receiving hollow element adapted for receiving one of said extension rods.

9. The implant as defined in claim 7, in combination with a vertebral column-repositioning instrument for use with said implant, said instrument further comprising:

a longitudinal member;

a first arm fixed to one end of said longitudinal member;

a second displaceable arm mounted on said longitudinal member for adjustable movement in the longitudinal direction of said longitudinal member and extending away from said longitudinal member in the same direction as said first arm;

support members hinged to said first and second arms, respectively; and a receiving hollow element mounted on each said support and adapted for receiving one of said extension rods;

wherein the hinge axis of each said support member runs approximately in a plane defined by said first and second arms and at an angle of inclination such that extensions of the hinge axes intersect on a side of the longitudinal member facing the support members.

10. The combination as claimed in claim 9, wherein the angle of inclination of each hinge axis is approximately 30° in relation to the longitudinal member.

11. The combination as claimed in claim 9, wherein said longitudinal member comprises a rack having teeth situated on a side facing away from said arms and spaced apart so that said hooks are insertable between said teeth.

12. The implant as claimed in claim 1, wherein the head of each anchoring screw and each connector have contacting surfaces which are configured as latching surfaces for latching the anchoring screw in a selected angular position about the longitudinal axis of the latching screw in said connector when the latching screw is tightened.

* * * * *